United States Patent
Van Berk

(10) Patent No.: US 6,550,327 B1
(45) Date of Patent: Apr. 22, 2003

(54) DEVICE FOR MEASURING THE DENSITY OF A FLOWING MEDIUM

(75) Inventor: Hendrikus Van Berk, Bunnik (NL)

(73) Assignee: De Groot Nijkerk Machinefabriek B.V., Nijkerk (NL)

(*) Notice: Subject to any disclaimer, the term of this patent is extended or adjusted under 35 U.S.C. 154(b) by 0 days.

(21) Appl. No.: 09/701,016

(22) PCT Filed: May 21, 1999

(86) PCT No.: PCT/NL99/00323

§ 371 (c)(1),
(2), (4) Date: Mar. 15, 2001

(87) PCT Pub. No.: WO99/61887

PCT Pub. Date: Dec. 2, 1999

(30) Foreign Application Priority Data

May 22, 1998 (NL) .............................................. 1009248

(51) Int. Cl.[7] .............................. G01N 9/26; E21B 47/00
(52) U.S. Cl. ..................................... 73/438; 73/152.18
(58) Field of Search ................................ 73/32 R, 438, 73/439, 446, 32 A, 323, 195, 196, 197, 152.18, 152.22, 152.29, 152.31, 152.51, 152.52

(56) References Cited

U.S. PATENT DOCUMENTS

| | | | | |
|---|---|---|---|---|
| 3,741,008 A | * | 6/1973 | Casey | 73/118 |
| 3,839,914 A | | 10/1974 | Modisette et al. | 73/438 |
| 3,981,202 A | * | 9/1976 | Spangle | 73/438 |
| 4,201,082 A | * | 5/1980 | Dockhorn et al. | 73/438 |
| 4,216,673 A | | 8/1980 | November | 73/861.03 |
| 4,274,283 A | * | 6/1981 | Maus et al. | 73/153 |
| 5,070,738 A | * | 12/1991 | Morgan | 73/863.83 |

FOREIGN PATENT DOCUMENTS

| | | |
|---|---|---|
| DE | 2031481 | 1/1971 |
| DE | 2821746 A1 | 11/1979 |
| WO | WO 9504869 | 2/1995 |

* cited by examiner

Primary Examiner—Helen Kwok
(74) Attorney, Agent, or Firm—Young & Thompson

(57) ABSTRACT

The device includes a pipe section in loop form having two arms which make an angle with the horizontal, which arms each contain two pressure sensors which are located some distance apart in the direction of flow, as well as a processing unit, connected to the pressure sensors, for determining the density of the medium on the basis of the pressures or an associated parameter measured by the sensors. The pipe section in loop form is connected in parallel to the pipeline.

7 Claims, 1 Drawing Sheet

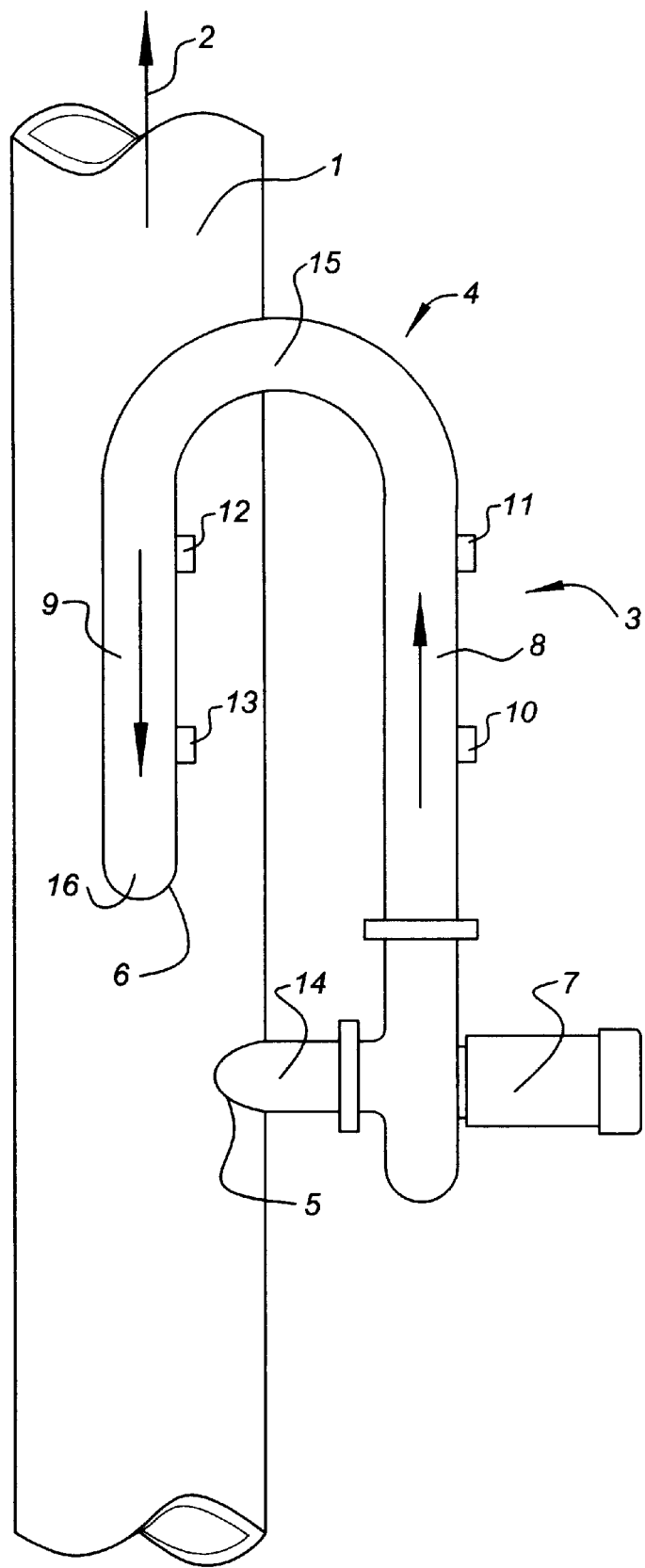

DEVICE FOR MEASURING THE DENSITY OF A FLOWING MEDIUM

FIELD OF THE INVENTION

The invention relates to a device for measuring the density of a flowing medium such as a mixture of water and particulate material, in a pipeline, comprising a pipe section in loop form having two arms which make an angle with the horizontal, which arms each contain two pressure sensors which are located some distance apart in the direction of flow, as well as a processing unit, connected to the pressure sensors, for determining the density of the medium on the basis of the pressures or an associated parameter measured by the sensors.

BACKGROUND OF THE INVENTION

A device of this type is disclosed in WO-A 95/04869. With this known device, the pipeline has a pipe section in loop form connected in series, which has approximately the same capacity (cross-sectional area) as the remainder of the pipeline. With this device the full flow of medium is fed through the pipe section in loop form.

In order to obtain a reliable measurement of the density, various conditions must be met. First of all the pressure sensors must be in a region of the arms of the pipe section in loop form where the flow is reasonably undisturbed. This means that they must be located in the straight section of the arms and, moreover, some distance away from the subsequent bend sections. This distance increases with the diameter of the pipeline.

Especially in the case of pipelines having a relatively large diameter, this leads to a section in loop form of appreciable dimensions, for example 5 to 12 meters high in the case of a vertical set-up of the arms. The cost of such a construction is appreciable.

SUMMARY OF THE INVENTION

The aim of the invention is to provide a device which does not have these disadvantages. Said aim is achieved in that the pipe section in loop form is connected in parallel to the pipeline.

Connecting the section in loop form in parallel offers the possibility of allowing the (main) pipeline itself to continue straight undisturbed. Only a faction of the flow of medium is diverted in order to perform a density measurement. As a consequence thereof, the cross-sectional dimension of the pipe section in loop form can remain restricted, which, in turn, has the consequence that the total height thereof can remain restricted. Nevertheless, a reliable density measurement can still be carried out in such a relatively small section in loop form since the flow has already become sufficiently quiescent a shorter distance away from the bend sections and has a relatively uniform character.

The connections from the pipe section in loop form to the pipeline can be some distance apart in the direction of flow of the medium through the pipeline. Incidentally, said connections can also be alongside one another.

To promote the measurement flow, the pipe section in loop form can contain a pump to promote the flow through the pipe section.

BRIEF DESCRIPTION OF THE DRAWING

The invention will be explained in more detail below with reference to an illustrative embodiment shown in the FIGURE.

DETAILED DESCRIPTION OF THE INVENTION

In the FIGURE, 1 indicates a pipeline through which a medium flows in the direction indicated by arrow 2. Said medium can be a mixture of for example, water and sand, such as is obtained during dredging work.

The device according to the invention, which is indicated in its entirety by 3, is connected to said pipeline 1. Said device 3 comprises a pipe section 4 in loop form which is connected by its feed 5 and discharge 6 to the pipeline 1. The discharge 6 is located in the direction of flow 2 downstream of the feed 5.

By means of a pump 7, a portion of the medium is pumped from the pipeline 1 into the pipe section 4 in loop form, in accordance with the arrows indicated here.

The pipe section in loop form has two essentially vertical arms 8, 9, in each of which sensors 10, 11 and, respectively, 12, 13 are located. Said sensors are suitable for measuring a pressure or a unit corresponding thereto in the medium flowing through the pipe section 4 in loop form.

The diameter of the arms 8, 9 is appreciably smaller than the diameter of the pipeline 1, which means that only a portion of the medium flows through the device 3.

The sensors 10–13 are positioned some distance away from the bend sections 14, 15, 16 of the pipe section 4 in loop form, so that a relatively undisturbed flow of medium prevails at the location of said sensors. By this means a reliable measurement is also ensured.

The sensors 10–13 are connected via leads, which are not shown, to a processing unit, which is known per se and is not shown, for processing the measured pressure data in the manner indicated below:

$$\Delta p_I = c \tfrac{1}{2} \rho v^2 + \rho_m g h$$

$$\Delta p_{II} = -c \tfrac{1}{2} \rho v^2 + \rho_m g h$$

$$\Delta p_I + \Delta p_{II} = 2 \rho_m g h$$

$$\rho_m = \frac{\Delta p_I + \Delta p_{II}}{2gh}$$

where:
 $\Delta p_I$=p11–p10
 $\Delta p_{II}$=p12–p13
 p10 to p13=pressure at the location of sensors 10 to 13
 g=acceleration due to gravity
 c=constant factor
 v=velocity of medium
 h=difference in height between sensors 11 and 10 and sensors 12 and 13
 ρ=density of medium In the FIGURE the pipeline 1 is shown in the vertical position. However, this is not necessary; the pipeline 1 can be in any position, including horizontal. The arms 8, 9 likewise do not have to be vertically oriented, but must be at a certain slope with respect to the horizontal.

What is claimed is:

1. A device for measuring the density of a flowing medium in a pipeline, the device comprising a pipe section in loop form having two arms which make an angle with the horizontal, each of the arms contains two pressure sensors located some distance apart in a direction of flow, as well as a processing unit, connected to the pressure sensors, for determining the density of the medium on the basis of pressures or an associated parameter measured by the sensors, the pipe section in loop form is connected in parallel to the pipeline, and wherein the pipe section in loop form is smaller in cross-sectional area than the pipeline.

2. The device according to claim 1, wherein connections from the pipe section in loop form to the pipeline are some distance apart in the direction of flow of the medium through the pipeline.

3. The device according to claim 1, wherein the pipe section in loop form contains a pump to promote the flow through the pipe section.

4. The device according to claim 1, wherein the arms of the pipe section in loop form are essentially vertically oriented.

5. The device according to claim 1, wherein the arms are identical in cross-sectional area.

6. The device according to claim 1, wherein the two arms are parallel to one another and are parallel to the pipeline so that flows of the medium through the arms and the pipeline are parallel.

7. The device according to claim 6, wherein the arms are parallel to the portion of the pipeline between connections from the pipe section to the pipeline.

* * * * *